United States Patent [19]

Thaler

[11] Patent Number: 4,700,729
[45] Date of Patent: Oct. 20, 1987

[54] LENS CLEANING DEVICE

[75] Inventor: Arnold Thaler, Plantation, Fla.

[73] Assignee: Windmere Corporation, Hialeah, Fla.

[21] Appl. No.: 796,717

[22] Filed: Nov. 12, 1985

[51] Int. Cl.[4] .............................................. B08B 3/02
[52] U.S. Cl. ..................................... 134/139; 134/143;
134/148; 134/153; 134/158
[58] Field of Search ............... 134/138, 139, 143, 148,
134/153, 154, 158, 184, 186, 196, 25.4, 33, 34;
206/5.1; 422/300, 301; 220/23, 234, 256, 304

[56] References Cited

U.S. PATENT DOCUMENTS

| | | | |
|---|---|---|---|
| 1,143,217 | 6/1915 | McGrath | 134/148 X |
| 1,962,376 | 6/1934 | Zarobsky | 220/256 |
| 2,062,704 | 12/1936 | Forsyth, Jr. | 134/138 X |
| 2,203,479 | 6/1940 | Witwer et al. | 134/196 X |
| 2,641,170 | 6/1953 | Hutchins | 134/138 |
| 2,712,826 | 7/1955 | Schleyer et al. | 134/139 |
| 2,721,567 | 10/1955 | Tierney | 134/158 |
| 2,823,682 | 2/1958 | Coulter | 134/94 |
| 3,041,212 | 6/1962 | Booth | 134/21 |
| 3,066,687 | 12/1962 | Rohmann | 134/148 |
| 3,113,579 | 12/1963 | Willis | 134/145 |
| 3,139,097 | 6/1964 | Hungerford et al. | 134/145 |
| 3,139,098 | 6/1964 | Hungerford et al. | 134/145 |
| 3,140,647 | 7/1964 | Miller | 134/138 X |
| 3,167,079 | 1/1965 | Weil | 134/137 |
| 3,343,657 | 9/1967 | Speshyock | 206/5.1 X |
| 3,379,200 | 4/1968 | Pennell | 134/143 |
| 3,444,868 | 5/1969 | Hungerford et al. | 134/143 |
| 3,567,064 | 3/1971 | Churan | 220/256 |
| 3,586,012 | 6/1971 | Paule | 206/5.1 X |
| 3,621,855 | 11/1971 | Rabinowitz | 206/5.1 X |
| 3,623,492 | 11/1971 | Frantz et al. | 206/5.1 |
| 3,643,672 | 2/1972 | Brown | 206/5.1 X |
| 3,770,113 | 11/1973 | Thomas | 134/143 X |
| 3,894,551 | 7/1975 | Stohlman | 134/135 |
| 3,939,968 | 2/1976 | Ryder | 206/5.1 |
| 4,009,777 | 3/1977 | Thomas | 206/5.1 |
| 4,223,782 | 9/1980 | Giambalvo | 206/5.1 |
| 4,396,583 | 8/1983 | LeBoeuf | 206/5.1 X |
| 4,444,307 | 3/1984 | Jermyn | 206/5.1 |

FOREIGN PATENT DOCUMENTS

| | | | |
|---|---|---|---|
| 458864 | 4/1928 | Fed. Rep. of Germany | 134/158 |
| 1011412 | 4/1952 | France | 134/138 |
| 1197161 | 7/1970 | United Kingdom | 206/5.1 |

Primary Examiner—Philip R. Coe
Attorney, Agent, or Firm—Dickstein, Shapiro & Morin

[57] ABSTRACT

A contact lens cleaning system having a chamber and a pump for generating streams of cleaning fluid within the chamber. The lenses are carried in lens retainers which rotate within the chamber and are exposed to the streams of cleaning fluid. The lens retainers are mounted on a single spindle held at both ends. The rotatable disposition of the lens retainers allow the lens to rotate and thus a greater extent if not essentially all of the surface area of the lens experiences the enhanced cleaning effect of the streams of cleaning fluid. The holding of the spindle at both ends insures that a uniform distribution of the impingement of cleaning fluid across the lens may be effected.

18 Claims, 5 Drawing Figures

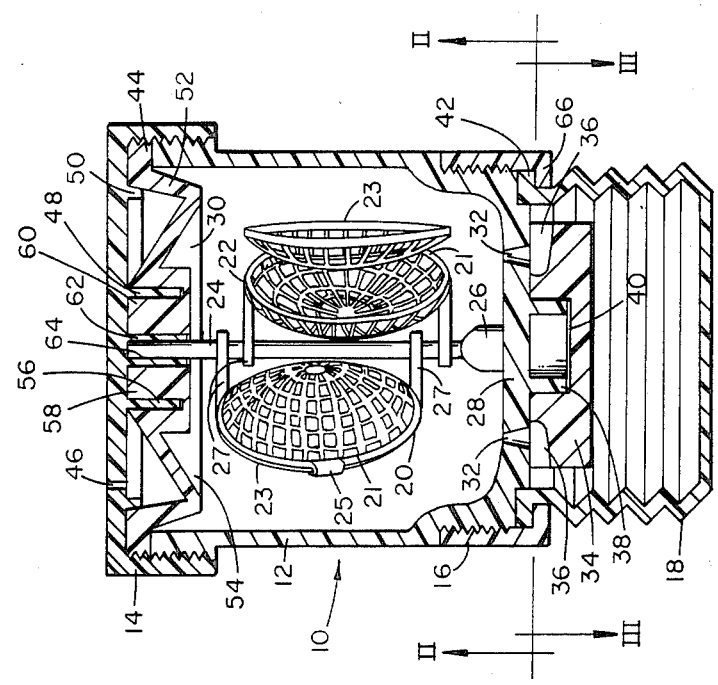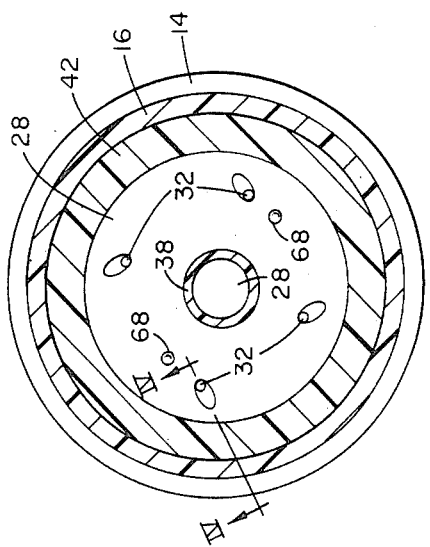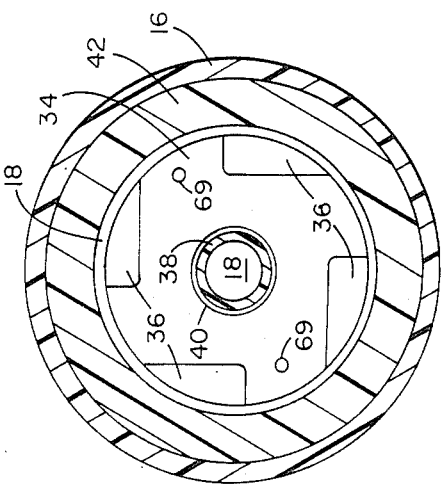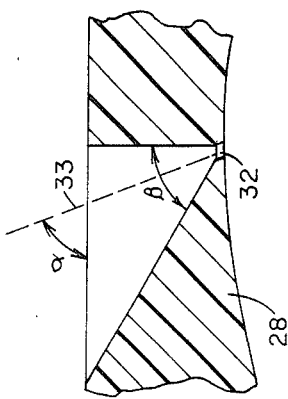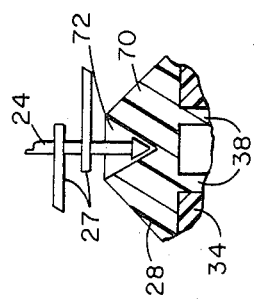

4,700,729

LENS CLEANING DEVICE

BACKGROUND

The present invention relates to a contact lens cleaning system in general and more particularly to a contact lens cleaning system wherein the lenses were cleaned by jets of water impinging on the contact lenses The cleaning of contact lenses, particularly the soft variety, must be undertaken with great care to insure that the contact lenses are not scratched or torn in the process. The soft contact lenses will tear if undue stress is placed on them. Moreover, the plastic material of the lenses will scratch easily if particles of dirt are rubbed across the surface.

One known system for cleaning contact lenses utilizes a plurality of streams of cleaning fluid directed on the lenses while the lenses are held essentially stationary. The disadvantage of this device is that the impingement of the streams the surface does not reach many parts of the surface of the contact lenses and the benefit of the cleaning action is not realized over the entire lens surface and the cleaning is therefore inefficient.

Another known type of system utilizes a carrier for contact lenses that is immersed into a cleaning fluid and agitated in the fluid to effect cleaning. The disadvantage of this type of device resides in the fact such cleaning action is inferior to the cleaning action of the jets of cleaning fluid impinging upon the lens.

SUMMARY OF THE INVENTION

The present invention alleviates the problems of the prior devices to a great extent by providing a lens cleaning system having a chamber, an irrigation means for generating at least one stream of cleaning fluid within the chamber, a lens retaining means for retaining at least one contact lens rotatably disposed within said chamber and exposed to at least a portion of said at least one stream of cleaning fluid, the lens retaining means including a spindle means and said at least one contact lens being rotatable about said spindle means, said spindle means being held at both ends.

The rotatable disposition of the lens retaining means allows the lens to rotate and thus a greater extent if not essentially all of the surface area of the lens experiences the enhanced cleaning effect of the at least one stream of cleaning fluid. Moreover, the holding of the spindle means at both ends insures that a uniform distribution across the lens may be effected. The means for holding the spindle at both ends is particularly advantageous for holding the spindle straight if the spindle has been warped or bent during the life of the device.

It is an object of the invention to provide a system for cleaning contact lenses.

It is another object of the present invention to provide a system for cleaning contact lenses which employs streams of cleaning fluid impinging upon the contact lens to be cleaned.

It is yet another object of the present invention to provide a device for cleaning contact lenses yielding the foregoing advantages and which disposes the contact lenses in rotatable suspension within the device.

It is yet another object of the present invention to provide a contact lense cleaner yielding the foregoing advantages and in which the contact lenses are held in a retaining means rotatably disposed of by the spindle and the spindle is held at both ends.

Other objects and advantages of the present invention will be readily apparent from the following description and drawings which illustrate the preferred embodiment of the invention.

BRIEF DESCRIPTION OF THE DRAWINGS

FIG. 1 is a cross-sectional elevation view of a lens cleaning system according to the present invention.

FIG. 2 is a view taken along section line II—II of FIG. 1.

FIG. 3 is a view taken along section line III—III of FIG. 1.

FIG. 4 is a view taken along section line V—V of FIG. 2.

FIG. 5 is a view of an alternate embodiment of a means to hold the lower end of the spindle.

DETAILED DESCRIPTION OF THE PREFERRED EMBODIMENT

Refer now to FIG. 1 wherein is shown a lens cleaning system, generally referred to by reference 10, according to the present invention. Lens cleaning device 10 includes a cleaning chamber 12 having a generally cylindrical housing wall 13 and a floor wall 28 at one end. Cap 14 screws onto the other end of housing wall 13 chamber 12 and has formed on its inside surface a first ring 50, a second ring 48 and a post 62. Post 62 has a recess 64. Spindle 24 extends into and is held in recess 64 of post 62 such as by adhesive or interference fit.

A contact lens retaining means is provided including lens carriers 20 and 22 each having a first basket half 21 and a second basket half 23 which are hingedly connected by hinge 25. Basket halves 21 of carriers 20 and 22 have supports 27 extending from diametrically opposed positions on their peripheries. Supports 27 are located approximately ninety degrees from the location of hinge 25 in the preferred embodiment. Supports 27 rotatably engage spindle 24 by apertures formed in supports 27.

The basket halves, hinge and supports of each of carrier 20 and 22 may be integrally molded or otherwise formed preferably from a flexible soft plastic material.

Bulb 26 is positioned or integrally formed at the end of spindle 24, opposite the end of spindle 24 inserted into recess 64 of post 62, so that carriers 20 and 22 are rotatably disposed between bulb 26 and post 62.

Bulb 26 has a surface on its bottom that mates with the surface of floor 28 so that spindle 24 is firmly held from excess movement with cap 14 snugly in place.

Seal 30 is disposed between cap 14 and housing wall 13 of chamber 12 and effectively seals the cap end of chamber 12 and has an annular lip 44 disposed between cap ring 50 and the cap threads. Lip 44 of seal 30 effectively seals the cap end of chamber 12 when cap 14 is tightened. Seal 30 has an annular seal portion 52 extending from the inner circumference of lip 44 converging conically into the chamber and away from cap 14 to form space 47 between cap 14 and seal 30. Seal 30 turns to extend converging conically back towards cap 14 by portion 54 which is connected to or intergrally formed with the central portion 56 as well as portion 32 of seal 30. Portion 56 has an aperture 60 for receiving post 62 and has recess 56 for receiving ring 48.

A pressure hole 46 is provided in cap 14 between rings 50 and 48. Hole 46 connects space 47 with the outside atmosphere. Preferably ring portion 48 and post 62 are slightly larger in dimension than recess 58 and aperture 60 respectively so that the elastomeric material of seal 30 will be compressed to some extent to form a seal against the passage of fluid between the contacting surfaces.

At the floor end of chamber 12, irrigation means is provided for generating at least one stream of cleaning fluid within chamber 12. The irrigation means includes a pump means including bellows 18 held in sealing engagement with the floor 28 of lens cleaning system device 10 by lip 66 of nut 16 engaging lip 42 of bellows 18 to form a fluid tight seal.

Floor 28 has a number of holes 32 which are formed therethrough at an angle from the normal to the plane of floor 28. An accelerator 34 has a number of accelerator channels 36 formed therein which are in fluid communications with corresponding accelerator channels 33 formed in floor 28. The profiles of accelerator channels 36 and 33 are preferably chosen such that the fluid flowing therethrough encounters a gradually decreasing crosssectional area and is correspondingly accelerated into a stream emerging from holes 32 of floor 28.

Accelerator 34 has a recess 40 for accepting post 38 extending from floor 28 to insure proper alignment of accelerator channels 36 with accelerator channels 33. Moreover, recesses 69 formed in accelerator 34 mate with posts 68 (FIGS. 2 and 3) to further insure proper alignment.

Refer now to FIG. 2 which shows a view of the underside of floor 28. Note that accelerator channels 33 are angled to direct the flow through holes 32 which are also angled to emerge from the floor 28 to impinge upon carriers 20 and 21 at an angle to cause the rotation of carriers 20 and 21 and the contact lenses carried therein about spindle 24.

Refer now to FIG. 3 which shows the top view of accelerator 34. Recesses 69 accept posts 68 (FIG. 2) to insure proper alignment so that accelerator channels 36 direct fluid into accelerator channels 32.

Refer now to FIG. 4 wherein is shown a cross-sectional view of accelerator portions 33 of floor 28. As shown in FIG. 4, the bellows 18 of cleaning system 10 is positioned above floor 28. Hole 32 is formed at an angle alpha with respect to the bottom surface of floor 28. Accelerator channel 33 is formed so that a fluid is converging upon and into hole 32 from both sides of its axis at an angle beta.

Refer now to FIG. 5 wherein is shown an alternate embodiment of the means to hold the bottom end of spindle 24 to the surface of floor 28. In this embodiment, floor 28 has a raised portion 70 that has recessed 72 and spindle 24 has a cone shaped bulb 73 that is accepted by recess 72 when cap 14 is screwed onto cleaning chamber 12. In this way, the spindle 24 is held from movement at its lower end proximate floor 28.

In operation of the device, cleaning fluid is placed into chamber 12 with cap 14 removed so that the fluid approximately fills bellows 18. More or less fluid can be used and preferrably the streams of cleaning fluid emerging from holes 32 strike the lenses and the lenses and carriers are free to rotate. Thus, preferrably, the level of cleaning fluid is below the carrier for substantially the duration of the stream of cleaning fluid.

The contact lenses are placed in carriers 20 and 22 and cap 14 is screwed into place whereupon bulb 26 engages floor 28 to hold spindle 24 against excess movement. The lenses are cleaned by compressing bellows 18 whereupon the increased pressure within bellows 18 causes fluid to flow through accelerator channels 36 and 32 to be accelerated therein and to emerge from holes 32 at an angle to floor 28 and impinging upon carriers 20 and 22 and the lenses carried thereby thus causing their rotation about spindle 24.

Pressure is relieved within the chamber by the flexing of seal 30 to collapse space 47 to some extent. The air in space 47 escapes through pressure hole 46. Upon release of the bellows, seal 30 relaxes back towards its original position drawing air back into hole 46 to fill space 47 and cleaning solution drains back through holes 32 into bellows 18.

The above description and drawings are only illustrative of one embodiment which achieves the objects, features and advantages of the present invention, and it is not intended that the present invention be limited thereto. Any modification of the present invention which comes within the spirit and scope of the following claims shall be considered part of the present invention.

What is claimed as new and desired to be secured by Letters Patent of the United States is:

1. A system for cleaning contact lenses comprising: a chamber; irrigation means for generating at least one stream of cleaning fluid within said chamber; lens retaining means for retaining at least one contact lens rotatably disposed within said chamber and exposed to at least a portion of said at least one stream of cleaning fluid at some position of rotation; and said lens retaining means including a spindle means for supporting said lens retaining means, said at least one contact lens being rotatable about said spindle means, said spindle means being held at both ends.

2. A system as in claim 1 wherein said irrigation means includes a wall having at least one aperture formed therein.

3. A system as in claim 2 wherein said irrigation means includes accelerator channel means for accelerating the cleaning fluid to form said at least one stream thereof having a decreasing flow area and having said aperture at its end.

4. A system as in claim 3 wherein said irrigation means includes pump means for pumping a supply of cleaning fluid through said accelerating channel means and through said at least one aperture to form said at least one stream of cleaning fluid.

5. A system as in claim 4 wherein said chamber includes a housing wall and a cap sealably engaging one end of said housing wall.

6. A system in claim 5 wherein said spindle means is held at one end to said cap.

7. A system as in claim 6 wherein said spindle means is held at its other end at said wall, said wall forming a floor of said chamber.

8. A system in claim 7 wherein said spindle has an enlarged bulb positioned at its floor end that engages said floor.

9. A system as in claim 8 wherein said bulb is contoured to be flush with said floor.

10. A system as in claim 8 wherein said bulb is tapered at its end and extends into a recess formed in said floor.

11. A system as in claim 10 wherein said floor has a raised portion, said recess being formed therein.

12. A systems as in claim 11 further comprising a cap sealing means for sealing said cap to said one end of said housing wall and including a seal contoured to form a space between said seal and said cap and a hole is formd in said cap to provide fluid communication between said space and the outside atmosphere to alleviate pressure variances in said chamber which may be caused by operation of said pump means.

13. A system as in claim 12 wherein said seal has a lip positioned between said cap and the cap end of said housing wall, an annular first seal portion extending from an inner circumference of said lip and converging conically into said chamber and away from said cap to form said space between said cap and said seal, a second annular seal portion extending converging conically back toward said cap and extending to a central portion of said seal, said cap having an inner surface and a first ring and a second ring and a post protruding from its inner surface, said first ring retaining said lip between said housing wall and said cap, said second ring extending into a recess formed in said seal central portion and said post extending through an aperture formed in said seal central portion, said spindle being held to said cap by insertion into a recess formed in said cap.

14. An apparatus for cleaning contact lenses comprising: a chamber; irrigation means for generating at least one steam of cleaning fluid within said chamber; lens retaining means for retaining at least one contact lens rotatably disposed within said chamber and exposed to at least a portion of said at least one stream of cleaning fluid at some position of rotation; said irrigation means including a wall having at least one aperture formd therein, accelerator channel means for accelerating the cleaning fluid to form said at least one stream thereof and having a decreasing flow area through said at least one aperture, and pump means for pumping a supply of cleaning fluid through said accelrating channel means and said at least one apertue to form said at least one stream of cleaning fluid.

15. An apparatus as in claim 14 wherein said pump means comprises a flexible housing sealably attached to said chamber.

16. An apparatus as in claim 15 wherein said wall is common to said chamber and said flexible housing.

17. An apparatus as in claim 16 wherein said aperture are angled with respect to said wall.

18. An apparatus for cleaning contact lenses comprising: irrigation means for generating at least one stream of cleaning fluid; a wall having at least one accelerating channel ending in an aperture formed in said wall at an angle thereto for directing said at least one stream of cleaning fluid; and lens retaining means for retaining at least one contact lens exposed to at least a portion of said at least one stream of cleaning fluid.

* * * * *